United States Patent
Ramsauer et al.

(10) Patent No.: US 7,653,179 B2
(45) Date of Patent: Jan. 26, 2010

(54) X-RAY FILTER ARRANGEMENT AND X-RAY FILTER THEREFOR

(75) Inventors: Martin Ramsauer, Pyrbaum (DE); Robert Standar, Pressfeld (DE)

(73) Assignee: Siemens Aktiengesellschaft, Munich (DE)

( * ) Notice: Subject to any disclaimer, the term of this patent is extended or adjusted under 35 U.S.C. 154(b) by 111 days.

(21) Appl. No.: 11/950,635

(22) Filed: Dec. 5, 2007

(65) Prior Publication Data
US 2008/0144775 A1 Jun. 19, 2008

(30) Foreign Application Priority Data
Dec. 14, 2006 (DE) .................. 10 2006 059 143

(51) Int. Cl.
*G21K 3/00* (2006.01)
(52) U.S. Cl. ..................................... 378/157
(58) Field of Classification Search .......... 378/156–158
See application file for complete search history.

(56) References Cited

U.S. PATENT DOCUMENTS

| 1,449,357 | A | * | 3/1923 | Waite | 378/98 |
| 2,405,444 | A | * | 8/1946 | Moreau et al. | 378/158 |
| 4,499,591 | A | * | 2/1985 | Hartwell | 378/62 |
| 6,418,193 | B1 | * | 7/2002 | Albagli | 378/158 |
| 6,851,854 | B2 | * | 2/2005 | Schmitt | 378/207 |
| 6,862,340 | B2 | * | 3/2005 | Wurzer | 378/157 |
| 7,092,490 | B2 | * | 8/2006 | Saladin et al. | 378/156 |

* cited by examiner

*Primary Examiner*—Edward J Glick
*Assistant Examiner*—Thomas R Artman
(74) *Attorney, Agent, or Firm*—Schiff Hardin LLP

(57) ABSTRACT

A filter arrangement for filtering x-rays particularly in a mammography apparatus, has a number of mountings, the mountings being provided for accommodation of one x-ray filter each. Each x-ray filter has a holding frame with a filter foil fastened therein, so the filter foil is mounted and demounted simply at the filter arrangement with the holding frame.

10 Claims, 1 Drawing Sheet

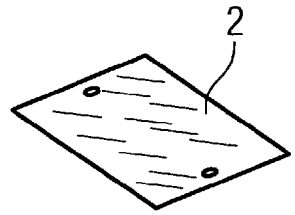
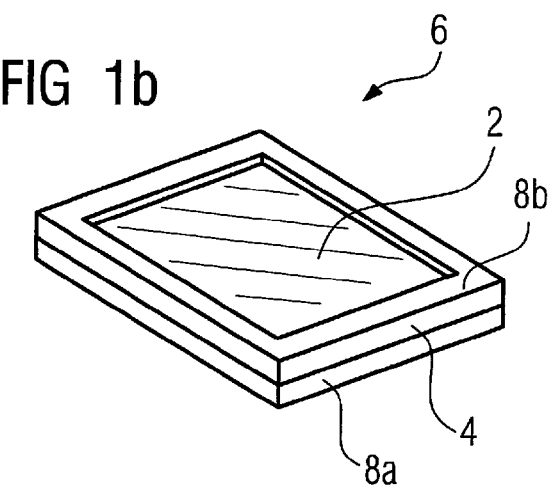
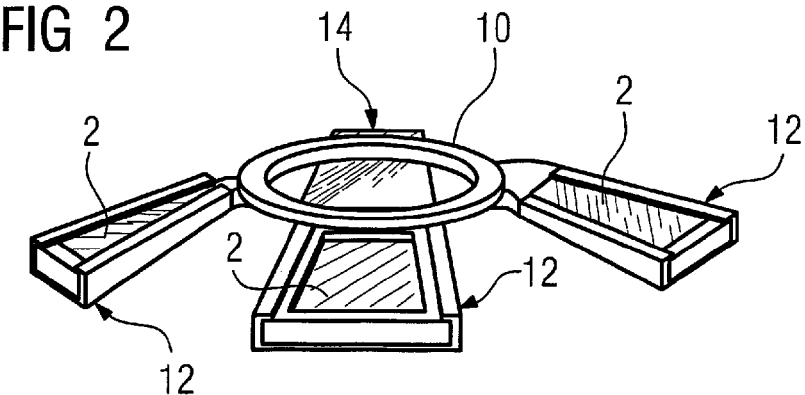
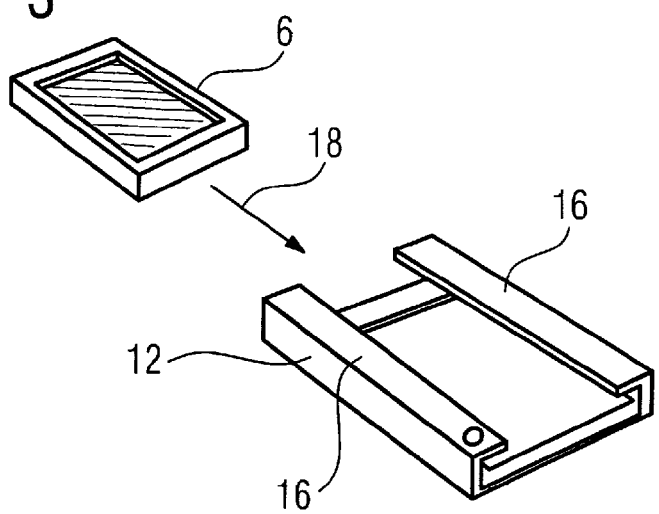

X-RAY FILTER ARRANGEMENT AND X-RAY FILTER THEREFOR

BACKGROUND OF THE INVENTION

1. Field of the Invention

The present invention concerns a filter arrangement for filtering x-rays, in particular for use in a mammography apparatus. The invention furthermore concerns an x-ray filter for such a filter arrangement.

2. Description of the Prior Art

Medical examinations of the soft tissue of the human breast that serve for early detection of breast cancer are implemented with x-ray radiation with a mammography apparatus. The breast to be examined is clamped between a subject table and a compression plate that can be shifted in position relative to the subject table. An x-ray examination is subsequently implemented with the irradiation unit, namely an x-ray radiator. A diaphragm is arranged to limit the x-ray beam by masking regions thereof. Furthermore, a filter arrangement, with typically a number of different filters, is provided between the x-ray radiator and the diaphragm. The individual filters serve for filtering out frequencies in the x-rays that are not required for the particular x-ray acquisition. An x-ray detector struck by the x-ray beam emitted from the irradiation unit strikes is integrated into the subject table. Soft x-ray radiation in the range below 50 kV (in particular under 30 kV) is used in the irradiation.

In the filter arrangement, filter foils made from various materials (for example rhodium or molybdenum) are glued onto a structure known as a filter wheel. In the case of a defective filter, an exchange is possible only with difficulty.

SUMMARY OF THE INVENTION

An object of the invention is to enable simple mounting and dismounting of a filter foil in a filter arrangement.

The object is inventively achieved by a filter arrangement for filtering x-rays, in particular in a mammography apparatus, having a number of mountings. The mountings are each provided for receiving and holding one x-ray filter. Each x-ray filter has a holding frame with a filter film fixed therein. The frame conforms to the mounting so as to fit therein.

The invention is based on the insight that a particularly simple mounting and dismounting of a filter foil is possible when the filter arrangement is fashioned not for a direct, firmly attached connection of the filter foil, but rather for accommodation of a removable x-ray filter containing the filter foil. The holding frame of the x-ray filter is fashioned from an essentially rigid material, such that it represents a type of carrier for the thin, flexible filter foil in which the filter foil is stretched. A significant advantage of such a filter arrangement is that the filter foil fixed in the holding frame is thus pre-tensioned and its installation at the mounting is thereby much simpler and faster. Moreover, affixing of the filter foil ensues with the holding frame and not directly at the filter foil, which offers the possibility to provide a positive connection (i.e. with a fastener) or non-positive connection (i.e. press fit or force fit) between the holding frame of the x-ray filter and the mounting of the filter arrangement in place of a material (bonded) connection. This connection is easy to release and thus the demounting of the x-ray filter is particularly simple.

To facilitate simple removal of the x-ray filter if it is damaged, the mounting is preferably fashioned to allow detachable holding of the x-ray filter.

In a preferred embodiment, the mounting is fashioned for accommodating the x-ray filter by insertion. The holding frame that supports the filter foil (and with it the x-ray filter) is fashioned so as to be dimensionally stable for this purpose. The insertion of the x-ray filter into the mounting represents a particularly simple embodiment for a positive connection between the x-ray filter and the filter arrangement. The mounting/dismounting of the x-ray filter requires very little work and time expenditure.

In order to enable a guided insertion of the x-ray filter into the mounting, according to a further preferred embodiment the mounting has two opposing slide guides. The slide guides can be fashioned as U-shaped or L-shaped profiles having a height that approximately corresponds to the thickness of the holding frame of the x-ray filter. Alternatively, the holding frame can be inserted into the mounting by being clipped therein.

To increase the operating safety in the use of the filter arrangement, in another embodiment the x-ray filter is securely held in the mounting and in particular is firmly connected therewith. The holding frame is hereby advantageously undetachably fastened in the mounting by a non-positive or positive connection. The non-positive or positive connection, for example, can be a bolt connection or a clamp spring.

In order to make the insertion of the filter foil into the holding frame easier, the holding frame is advantageously fashioned in two parts and has an upper part and a lower part between which the thin filter foil is stretched. The two parts can be connected with one another by a positive connection, for example by mechanically engaging in one another.

The holding frame is preferably expediently fashioned such that the filter foil is clamped (pinched) therein. The filter foil, for example, is clamped between the two parts of the holding frame and thus is held in a fixed position. Alternatively, accommodation elements can be provided at one of the two parts of the holding frame at which the filter foil is pre-tensioned, for example by suspension or by screwing before the two parts are brought together.

The holding frame is preferably an injection-molded part made of plastic. The holding frame can be designed easily and rigidly by a suitable selection of the plastic. Moreover, the shaping of plastic requires no great effort, so the holding frame can be produced simply and inexpensively.

In order to avoid transposing the different filter foils (respectively composed of various materials) in the mounting at the filter arrangement, the individual holding frames are advantageously characterized differently; particularly they can exhibit different colors. A separate color of the holding frame is associated with each foil type.

The above object is furthermore achieved in accordance with the invention by an x-ray filter as described above. The advantages and preferred embodiments described above with regard to the filter arrangement are also applicable to the x-ray filter.

The x-ray filter is advantageously provided both for exchangeable attachment in a test mounting for quality testing of the filter foil, and for exchangeable attachment in a mounting of the filter arrangement for actual use. The quality testing ensues before the actual use of the x-ray filter in a mammography apparatus, for example while it's still at its manufacturing site. A simple and secure handling of the x-ray filter is ensured via the universal usability of the x-ray filter both in the test mounting and in the mounting of the filter arrangement. Since, due to the holding frame, the filter foil does not have to be directly contacted during the quality testing, the probability of a damaging of the filter foil is significantly reduced. The x-ray filter is thus mounted and dismounted at the test mounting quickly and without great effort for quality control. After the quality control it is used in a mammography apparatus without alterations to its assembly.

BRIEF DESCRIPTION OF THE DRAWINGS

FIG. 1a shows a filter foil, and FIG. 1b shows the filter foil held in a filter frame to form an x-ray filter in accordance with the present invention.

FIG. 2 shows a filter arrangement in accordance with the present invention.

FIG. 3 illustrates an embodiment for mounting the x-ray filter in the filter arrangement in accordance with the present invention.

DESCRIPTION OF THE PREFERRED EMBODIMENTS

In FIG. 1a a filter foil 2 is shown that is used in a mammography apparatus (not shown in detail) for filtering x-rays. The filter foil is in particular fashioned from rhodium or molybdenum and exhibits a thickness of a few μm and has an area of approximately 30×35 mm. The filter foil 2 is stretched in a holding frame 4 before its use, both for its use in a mammography apparatus and preferably also for a quality testing. The filter foil 2 and the holding frame 4 together form an x-ray filter 6 that is shown in FIG. 1b. The holding frame 4 is fashioned in two parts and has a lower part 8a and an upper part 8b. Both parts 8a, 8b are injection-molded parts made from a plastic that, in the exemplary embodiment, are fashioned complementary to one another such that they engage in one another in the assembled state of the x-ray filter 6 and thereby clamp the filter foil 2 therebetween.

The x-ray filter 6 is held on a filter arrangement 10 that is shown in FIG. 2. In this exemplary embodiment the filter arrangement 10 is fashioned as a type of filter wheel that has three mountings 12 for x-ray filters 6 as well as a mirror 14 angled at approximately 35° (the angle is dependent on the position of a light source that, as is known, generates an illumination beam). The mirror 14 allows the x-ray field to be checked on the patient surface by means of a light source (not explicitly shown here; in particular a light bulb-generated illumination ray) before the actual x-ray acquisition by the illumination ray being deflected by the mirror 14 in the direction toward the x-ray field. In this exemplary embodiment an x-ray filter 6 with one filter foil 2 made from molybdenum as well as two x-ray filters 6 with filter foils made from rhodium of different thicknesses are fastened in the three mountings 6.

Each of the mountings 12 has two opposing slide guides 16 that are fashioned in the manner of tracks bent into an L-shaped cross-section. The x-ray filter 6 is slid into the slide guides 16, which is indicated with the arrow 18 in FIG. 3. The attachment of the x-ray filter 6 can alternatively or additionally ensue by catch projections that catch in corresponding recesses at the mountings and thus positively connect the holding frames 4 with the mountings. After the insertion of the x-ray filter 6 into the mounting 12, the two firmly connect with one another (for example by connection such as bolting) so that the x-ray filter 6 cannot slide out from the mounting 12 in operation of the filter arrangement 10. The connection between the x-ray filter 6 and the mounting 12 is detachable, such that an exchange of the x-ray filter 6 ensues quickly and in a simple manner in the event that the filter foil 2 is damaged and thus the x-ray filter 6 must be exchanged.

The x-ray filter 6 can simultaneously also be inserted into a test mounting that is used for the purpose of the quality control of the x-ray filter 6. The test mounting is designed identical to the mounting 12 and arranged in a testing device. After quality testing, the x-ray filters 6 are removed and can be used without adaptations or alterations in a filter arrangement 10 as is to be learned from FIG. 2.

Furthermore, the individual holding frames 4 can be characterized differently, in particular colored differently, so that the exchange certainty is increased both in the testing and in the mounting.

Although modifications and changes may be suggested by those skilled in the art, it is the intention of the inventors to embody within the patent warranted hereon all changes and modifications as reasonably and properly come within the scope of their contribution to the art.

We claim as our invention:

1. A filtering arrangement for filtering x-rays comprising:
   a mounting structure comprising a plurality of individual mountings;
   a plurality of x-ray filters, each x-ray filter comprising a holding frame with a filter foil fastened therein, said filter foil being comprised of a material that filters x-rays;
   the holding frame of each x-ray filter conforming in shape and size to a shape and size of the respective mountings, with one of said x-ray filters being received and held in a respective one of said mountings; and
   the holding frame of each x-ray filter comprising a first frame part having a first shape and a second frame part having a second shape that is complementary to said first shape, said first and second frame parts being engaged by said complementary shape, with the x-ray filter clamped therebetween.

2. A filter arrangement as claimed in claim 1 wherein the respective x-ray filters are detachably fixed in the respective mountings.

3. A filter arrangement as claimed in claim 2 wherein each mounting structure comprises spaced-apart, opposing slide guides that slidably receive therebetween said first and second frame parts with said x-ray filter clamped between said first and second frame parts.

4. A filter arrangement as claimed in claim 1 wherein each of said mountings has an open end, and wherein the respective x-ray filters are insertable into the respective mountings via the open end thereof.

5. A filter arrangement as claimed in claim 4 wherein each of said mountings comprises two opposing slide guides between which said x-ray filter is slid and held.

6. A filter arrangement as claimed in claim 1 wherein the holding frame of each of said x-ray filters is none-detachably held in the respective mountings by a force fit connection.

7. A filter arrangement as claimed in claim 1 wherein the holding frame of each of said x-ray filters is none-detachably held in the respective mountings by a fastened connection.

8. A filter arrangement as claimed in claim 1 wherein each holding frame is an injection-molded part comprised of plastic.

9. A filter arrangement as claimed in claim 1 wherein each holding frame has an identifying characteristic that identifies the material of the filter foil thereof, the identifying characteristics of the respective x-ray filters being different.

10. A filter arrangement as claimed in claim 9 wherein said respectively different filter characteristics are different colors.

* * * * *